(12) United States Patent
Rust

(10) Patent No.: US 9,968,639 B2
(45) Date of Patent: May 15, 2018

(54) STEM CELLS AND PANCREATIC CELLS USEFUL FOR THE TREATMENT OF INSULIN-DEPENDENT DIABETES MELLITUS

(71) Applicant: Seraxis, Inc., Germantown, MD (US)

(72) Inventor: William L. Rust, Germantown, MD (US)

(73) Assignee: Seraxis, Inc., Germantown, MD (US)

( * ) Notice: Subject to any disclaimer, the term of this patent is extended or adjusted under 35 U.S.C. 154(b) by 476 days.

(21) Appl. No.: 13/925,248

(22) Filed: Jun. 24, 2013

(65) Prior Publication Data

US 2013/0344594 A1 Dec. 26, 2013

Related U.S. Application Data

(60) Provisional application No. 61/664,259, filed on Jun. 26, 2012.

(51) Int. Cl.
*A61K 35/39* (2015.01)
*C12N 5/071* (2010.01)

(52) U.S. Cl.
CPC ............ *A61K 35/39* (2013.01); *C12N 5/0676* (2013.01); *C12N 5/0678* (2013.01); *C12N 2500/05* (2013.01); *C12N 2500/25* (2013.01); *C12N 2500/30* (2013.01); *C12N 2500/38* (2013.01); *C12N 2500/42* (2013.01); *C12N 2501/115* (2013.01); *C12N 2501/117* (2013.01); *C12N 2501/15* (2013.01); *C12N 2501/385* (2013.01); *C12N 2501/41* (2013.01); *C12N 2501/60* (2013.01); *C12N 2506/22* (2013.01); *C12N 2506/45* (2013.01)

(58) Field of Classification Search
None
See application file for complete search history.

(56) References Cited

U.S. PATENT DOCUMENTS

| | | |
|---|---|---|
| 6,436,704 B1 | 8/2002 | Roberts |
| 6,815,203 B1 | 11/2004 | Bonner-Weir et al. |
| 7,544,510 B2 | 6/2009 | Habener et al. |
| 7,604,991 B2 | 10/2009 | Bouwens |
| 8,110,399 B2 | 2/2012 | Habener et al. |
| 8,377,689 B2 | 2/2013 | Tsang et al. |
| 8,455,251 B2 | 6/2013 | Ra et al. |
| 2002/0077309 A1 | 6/2002 | Walker et al. |
| 2004/0115805 A1 | 6/2004 | Tsang et al. |
| 2006/0029987 A1 | 2/2006 | Domon et al. |
| 2010/0204258 A1 | 8/2010 | Harris et al. |
| 2011/0111499 A1 | 5/2011 | Torihashi et al. |
| 2011/0281355 A1 | 11/2011 | Xu |

FOREIGN PATENT DOCUMENTS

| | | |
|---|---|---|
| WO | WO 01/77300 A2 | 10/2001 |
| WO | WO 2009/061024 A1 | 5/2009 |
| WO | WO 2009/128533 A1 | 10/2009 |
| WO | WO 2009/136168 A1 | 11/2009 |
| WO | WO 2011/143299 A2 | 11/2011 |

OTHER PUBLICATIONS

Ciba et al., "In vitro cultures of human pancreatic stem cells: Gene and protein expression of designated markers varies with passage," Ann. Anat., 2009, 191(1), 94-10.
Dang et al., "Enhanced function of immuno-isolated islets in diabetes therapy by co-encapsulation with an anti-inflammatory drug," Biomaterials, 2013, 34, 5792-5801.
Dor et al., "Adult pancreatic β-cells are formed by self-duplication rather than stem-cell differentiation," Nature, 2004, 429(6987), 41-4.6.
Gong et al., "Islet-derived stem cells from adult rats participate in the repair of islet damage," J. Mol. Histol., 2012, 43(6), 745-750.
Kroon et al., "Pancreatic endoderm derived from human embryonic stem cells generates glucose-responsive insulin-secreting cells in vivo," Nat. Biotechnol., 2008, 26(4), 443-452.
Lai, M.I., "Advancements in reprogramming strategies for the generation of induced pluripotent stem cells," J. Assist. Reprod. Genet., 2011, 28, 291-301.
Matveyenko et al., "Inconsistent formation and nonfunction of insulin-positive cells from pancreatic endoderm derived from human embryonic stem cells in athymic nude rats," Am. J. Physiol. Endocrinol. Metab., 2010, 299, E713-720.
Nakagawa et al., "Promotion of direct reprogramming by transformation-deficient Myc," Proc. Natl. Acad. Sci. U S A, 2010, 107(32), 14152-14157.
Noguchi, Hirofumi, "Pancreatic stem/Progenitor Cells for the Treatment of Diabetes," Cell Transplant., 2010 19(6), 879-886.
Pagliuca et al., "How to make a functional β-cell," Dev., 2013, 140, 2472-2483.
Plath et al., "Progress in understanding reprogramming to the induced pluripotent state," Nat. Rev. Genet., 2011, 12(4), 253-265.
Rezania et al., "Maturation of Human Embryonic Stem Cell-Derived Pancreatic Progenitors into Functional Islets Capable of Treating Pre-existing Diabetes in Mice," Diabetes, 2012, 61(8), 2016-2029.
Robertson, R.P., "Update on Transplanting Beta Cells for Reversing Type 1 Diabetes," Endocrinol. Metab. Clin. N. Am., 2010, 39, 655-667.
Rust et al., "Three-Dimensional Extracellular Matrix Stimulates Gastrulation in Human Enbryoid Bodies," Stem. Cells Dev., 2006, 15(6), 889-904.

(Continued)

*Primary Examiner* — Blaine Lankford
(74) *Attorney, Agent, or Firm* — Foley & Lardner LLP

(57) ABSTRACT

Fresh human pancreas tissue can be used as a source of cells when to identify and select a non-stem cell population that is predisposed to be a source for surrogate pancreatic cells that can be used in treating insulin-dependent diabetes. The progenitors of these surrogate pancreatic cells have no reprogramming genes integrated into their genomes, differentiate to the pancreatic lineage pursuant to a protocol that employs only defined reagents, and are substantially unable to differentiate to the mesodermal lineage.

12 Claims, 7 Drawing Sheets

(56) References Cited

OTHER PUBLICATIONS

Shapiro, A.M., "Strategies toward single-donor islets of Langerhans transplantation", Curr. Opin. Organ Transplant., 2011, 16(6), 627-631.

Stover et al., "The Generation of Embryoid Bodies from Feeder-Based or Feeder-Free Human Pluripotent Stem Cell Cultures," Methods Mol. Biol., 2011, 767, 391-398.

Tahamtani et al., "Treatment of Human Embryonic Stem Cells with Different Combinations of Priming and Inducing Factors Toward Definitive Endoderm," Stem Cells and Dev., 2013, 22(9), 1419-1432.

Takacs et al., "Epigenetic regulation of latent Epstein-Barr virus promoters," Biochim Biophys Acta, 2010, 1799(3-4), 228-235, abstract.

Takahashi et al., "Induction of Pluripotent Stem Cells from Mouse Embryonic and Adult Fibroblast Cultures by Defined Factors," Cell, 2006, 126(4), 663-676.

Wade-Martins, Richard, "Developing Extrachromosomal Gene Expression Vector Technologies: An Overview," Methods in Molecular Biology, 2011, 738:1-17.

Xu et al., "Global Expression Profile of Highly Enriched Cardiomyocytes Derived from Human Embryonic Stem Cells," Stem Cells, 2009, 27(9), 2163-2174.

Yamanaka, S., "Induced Pluripotent Stem Cells: Past, Present, and Future," Cell Stem Cell, 2012, 10, 678-684.

Yi et al., "Betatrophin: A Hormone that Controls Pancreatic β Cell Proliferation," Cell, May 9, 2013, 153:1-12.

Donghui Zhang et al., "Highly Efficient Differentiation of Human ES Cells and iPS Cells into Mature Pancreatic Insulin-Producing Cells", *Cell Research*, Apr. 1, 2009, vol. 19, No. 4, pp. 429-438.

International Search Report and Written Opinion of the International Searching Authority dated Oct. 4, 2013 issued in PCT/US2013/047243.

Written Opinion of the International Preliminary Examining Authority dated Jun. 17, 2014 issued in PCT/US2013/047243.

Jan Jensen et al., "Independent Development of Pancreatic α- and β-Cells from Neurogenin3-Expressing Precursors. A Role for the Notch Pathway in Repression of Premature Differentiation", *Diabetes*, Feb. 1, 2000, vol. 49, No. 2, pp. 163-176.

Junying Yu et al., "Human Induced Pluripotent Stem Cells Free of Vector and Transgene Sequences", *Science*, May 8, 2009, vol. 324, pp. 797-801, and Erratum postdate Jun. 5, 2009.

Qiao Zhou et al., "In Vivo Reprogramming of Adult Pancreatic Exocrine Cells to β-Cells", *Nature*, Oct. 2, 2008, vol. 455, pp. 627-632.

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggcaacctgg agaatttgtt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccggttaca gaaccacact                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tacctcagcc tccagcagat                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgcgtcacac cattgctatt                                              20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccagaatcca gacctgcaca a                                            21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctctgcctcc tccacgaa                                                18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtagcgctgc aaacaatgaa                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccaacagcc tgagaaatc                                                19

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggagcggtga agatggaa                                                 18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacgtgttca tgccgttcat                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaattacaa cccctacatc                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagtttcact cctggccact                                               20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agtgctgagg cctacctcct                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagaaatgc agccgagtag                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gccctgacca ctccagttta                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagtcctgg atttccttcc                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccccagggt tatgagacta                                              20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtccagcttg gaggacctt                                               19
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggaccctag agccgaaaag                                                   20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttgtccgcc tcgtcttct                                                    19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggaagcccaa gaacctgaat                                                   20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggaggaagg ctctcactg                                                    19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attgctgaaa ccgagaatgg                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgctccttga ggttgaaaag                                                   20

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caatgtggcc gaggactttg                                                20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cattctcctt agagagaagt gg                                             22
```

STEM CELLS AND PANCREATIC CELLS USEFUL FOR THE TREATMENT OF INSULIN-DEPENDENT DIABETES MELLITUS

CROSS-REFERENCE TO RELATED PATENT APPLICATIONS

This application claims priority from U.S. provisional application No. 61/664,259, filed Jun. 26, 2012, the contents of which are incorporated here by reference in its entirety.

SEQUENCE LISTING

The instant application contains a Sequence Listing which has been submitted electronically in ASCII format and is hereby incorporated by reference in its entirety. Said ASCII copy, created on May 6, 2015, is named 105305-0102_SL.txt and is 6,227 bytes in size.

BACKGROUND OF THE INVENTION

A. Unmet Need for Pancreatic Endocrine Cells

Insulin-dependent diabetes is a disease characterized by a loss of the insulin producing cells of the pancreas. The insulin producing cells, also called "beta" cells, normally reside in small spherical structures termed "islets of Langerhans," which are dispersed throughout the pancreas. It is proven in humans and animals that the transplant of replacement islets of Langerhans, containing functional beta cells, can cure insulin-dependent diabetes. In this procedure, islets are purified from the pancreata of one or more deceased organ donors and injected into one of various sites in the body. Some islets survive the procedure and establish residency in the body where they make and secrete insulin. This can suffice to cure the patient for a few years, until the end of the lifespan of the transplanted islets. See Shapiro (2011) and Robertson (2010).

Although this process effectively treats diabetes, there are insufficient donor pancreata to treat more than a tiny fraction of diabetic patients. For this reason alternative sources of beta cells or pancreatic islets are needed.

B. Alternative Source of Pancreatic Cells

A prospective source of replacement pancreatic cells that has garnered much attention is pluripotent stem cells. Pluripotent stem cells are harvested from an embryo, or they can be created artificially by directing fully differentiated somatic cells to an embryonic-like state; that is, by "reprogramming" adult cells to resemble cells that are harvested from an embryo. Whether by harvesting or reprogramming, all pluripotent stem cells share three characteristics:

Expression of stem cell genes: They express genes typically expressed in the early mammalian embryo.

Immortality: They can be expanded in culture to theoretically unlimited quantities.

Maturation into all lineages of the mammalian body: All adult organs are derived from one of three tissue lineages of the early embryo. These are endoderm, from which the pancreas and other gut organs are formed, mesoderm, from which muscle and skeleton are formed, and ectoderm, from which brain and skin are formed.

See Yamanaka (2012), Plath (2011), Lai, (2011), and Stover (2011).

Protocols have been devised to manipulate pluripotent stem cells to form pancreatic cells. Some of these protocols are capable of driving the differentiation of pluripotent stem cells to a form resembling that of fetal progenitors of the islets of Langerhans. See Kroon (2008), and Rezania (2011). None yields pancreatic cells, however, that are capable of further maturation into functional, insulin-producing cells that could be used therapeutically, in the manner mentioned above.

Conventional protocols for obtaining pancreatic progenitors have a number of drawbacks and disadvantages, but key among them are these:

The populations of pancreatic progenitors are impure, being contaminated by non-pancreatic cells. Pluripotent stem cells are predisposed to form all three germ layers. Therefore, even the most efficient protocol produces populations of pancreatic cells intermixed with non-pancreatic cells.

The populations of pancreatic progenitors are contaminated by immature cells. These cells have retained the property of immortality and can initiate a tumor after transplant to a patient.

The pancreatic progenitors fail to mature into fully functional insulin producing beta cells.

The protocols for culturing the cells employ reagents and procedures that regulatory agencies generally do not accept for human use.

See Matveyenko (2010), Tahamtani (2013). See also Title 21, U.S. Code of Federal Regulations, part 1271.

C. Cellular Heterogeneity of the Adult Pancreas

Islets originate during embryogenesis from progenitor cells that bud off from the developing pancreatic ducts. During the life of a healthy individual, beta cells are produced exclusively through replication of existing beta cells. See Dor (2004). The process of beta cell replication occurs more quickly during periods of weight gain, pregnancy, and recovery following pancreatic injury. Isolated beta cells have not replicated in culture heretofore without losing their mature properties. See Pagluca (2013).

Pancreatic stem cells or progenitor cells have not been identified in mature tissue through lineage tracing experiments. Nevertheless, a number of publications have described cells, isolated from the mammalian pancreas, that are said to display some stem cell characteristics. These cells have been identified in the ductal tissue, in the exocrine tissue, and in the islets themselves. For instance, see Gong (2012), Noguchi (2010), and Ciba (2009). They are described as having limited replicative ability and being induced to express insulin.

In addition, a number of published patent documents describe adult stem cells said to be harvested directly from the mature pancreas. See U.S. Pat. No. 6,436,704, U.S. Pat. No. 6,815,203, U.S. Pat. No. 7,544,510, U.S. Pat. No. 8,110,399 and U.S. Pat. No. 8,377,689, and also published U.S. application No. 2004/0115805.

These cell populations have not been manufactured at a scale required to treat a patient, and none has been shown to secrete insulin appropriately in response to glucose. For these reasons, these cells populations have not shown clinical benefit.

For example, U.S. Pat. No. 8,377,689 speaks of pancreatic cells that are said to replicate in culture and to be induced to express insulin. As described, however, these cells had limited replicative ability and did not mature into fully functional beta cells or, at least, were incapable of reversing diabetes in rodent models. That is, the results actually obtained are said to show, in a "diabetic mouse" model, "a recovery from . . . hyperglycemia (>400 mg/dl) to near normal (<300 mg/dl) within five weeks, while the non-transplanted diabetic mouse was hyperglycemic throughout the study period." Column 45, after line 18 et seq. (emphasis added). In the diabetic mouse model, however, a "normal" is about 150 mg/dl, while a persistent reading above 250 mg/dl, as was reported, is considered proof of a stable diabetic state. See Dang (2013), for example.

Thus, the potential of strategies for curing diabetes by the transplant of surrogate beta cells or islets of Langerhans has gone largely unrealized for want of a scalable source of pharmaceutical-grade therapeutic pancreatic cells.

This body of work is distinct from the invention described here because it pertains to the isolation of a stem cell from a mammalian pancreas. This invention pertains to the isolation of a fully mature, non-stem cell from a pancreas or other source that is manipulated in culture to adopt stem cell characteristics. This method relies on harnessing the genetic diversity of mature cells within human organs to identify the subpopulation that can be manipulated to become a therapeutically useful stem cell. The genetic diversity of cells present in mature human tissues has been appreciated only recently, and conventional understanding is incomplete regarding cell heterogeneity within the mature pancreas.

SUMMARY OF THE INVENTION

As noted, current techniques for creating pancreatic cells do not yield effective surrogate pancreatic cells, i.e., cells that can be transplanted to a site in the mammalian body where they establish residency and perform a function of a native pancreatic cell. The present invention overcomes this shortcoming and other disadvantages by providing surrogate pancreatic cells and cell-containing compositions that are pharmaceutical-grade, i.e., that the U.S. Food and Drug Administration (FDA) and/or other such regulatory agencies deem acceptable for human use. For example, see Title 21, U.S. Code of Federal Regulations, part 1271], the contents of which are incorporated here by reference in its entirety.

With respect to human cell therapy generally, the acceptability criteria of regulatory agencies worldwide emphasize the safety and effectiveness of the cells employed. Central safety concerns in this context are (i) the tendency of the cells to form a tumor and (ii) the risk of transferring toxic, immunogenic, or infectious particles from animal-derived reagents, which the cells may have contacted. Effectiveness criteria include that the cell population be potent for the given cellular function and stable over the effective treatment period.

Accordingly, a surrogate pancreatic cell-containing composition of the invention (1) does not contain non-therapeutic cells that decrease potency or perform unwanted functions, but its constituent therapeutic cells (2) are cultured using defined, non-animal-origin components, according to internationally accepted standards, and (3) are not genetically modified, transformed, karyotypically abnormal, or otherwise characterized by an unacceptably high risk of instability or tumorigenicity.

In accordance with one of aspect of the invention, therefore, a composition is provided that comprises non-pluripotent progenitors of surrogate pancreatic cells. The progenitors (i) have no reprogramming genes integrated into their genomes, (ii) differentiate to the pancreatic lineage pursuant to a protocol that employs only defined reagents, and (iii) are substantially unable to differentiate to the mesodermal lineage.

A method also is provided, according to another aspect of the invention, for generating a composition comprising such non-pluripotent progenitors of surrogate pancreatic cells that are suitable for treating insulin-dependent diabetes. The inventive method comprises:
 a. harvesting human cells from viable human pancreatic tissue in minimal, defined culture conditions;
 b. culturing the primary human cells for a period of days that is fewer than about 9 days; then
 c. using reprogramming genes to reprogram primary human cells from (b) such that reprogrammed cells are obtained that have no reprogramming genes integrated genomically but that do have a stem cell morphology;
 d. firstly selecting among the reprogrammed cells obtained in (c) for an ability to proliferate, without losing the stem cell morphology, in minimal, defined culture conditions whereby proliferating reprogrammed cells are obtained; and then
 e. secondly selecting from among the proliferating reprogrammed cells for a cell population characterized by (i) an ability to survive and differentiate to the pancreatic lineage in the course of a protocol that employs only defined reagents, and (ii) a substantial inability to differentiate to the mesodermal lineage,
whereby the above-mentioned non-pluripotent progenitors are obtained.

Another aspect of the invention concerns a composition comprising surrogate pancreatic cells, suitable for treating insulin-dependent diabetes, where (A) the surrogate pancreatic cells are derived from the non-pluripotent progenitors described above and (B) more than about 90% of cells comprising the composition express the markers Pdx1, Nkx6.1, and NeuroD1. The invention further provides a method for generating such surrogate pancreatic cells, which method comprises:
 a. exposing the non-pluripotent progenitors to a first combination of components that drive differentiation to the endodermal lineage, whereby endodermal cells are obtained, the first combination excluding serum and any wnt family member; and then
 b. exposing the endodermal cells to a combination of components that drive differentiation to the pancreatic endocrine lineage,
whereby the surrogate pancreatic cells in question are obtained.

DETAILED DESCRIPTION OF THE PREFERRED EMBODIMENTS

Figure 1:
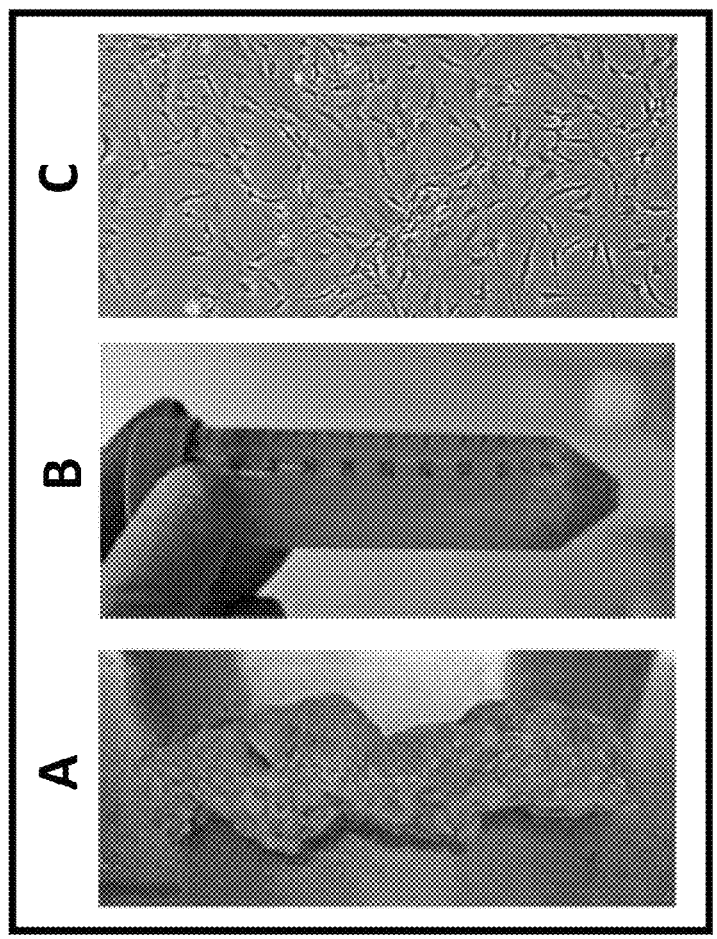
FIG. 1 depicts harvesting of cells from a human organ. That is, a viable human pancreas is minced into fragments (A), which then are rinsed and sedimented in a conical tube (B). Adherent cells (C) are obtained after 72 hours in culture. In the defined culture conditions provided, the cell cultures respectively comprised a mixed population of cells, which exhibit epithelial and fibroblastic morphologies. There was no evidence of stem cell or mesenchymal cell morphologies

A. Inventive Approach to Supplying Pharmaceutical-Grade Surrogate Pancreatic Cells Among the diversity of cells present within the adult pancreas, a subpopulation of cells has been discovered that can be exploited for the derivation of a therapeutic cell, as described above. These cells are not pancreatic stem cells or progenitor cells, but rather are members of a mature cell population of diverse genetic composition that harbor a specific genetic character rendering them amenable to the manipulations described in detail below. Accordingly, a key aspect of the invention is the harvesting of cells from an adult organ such that a diverse population is maintained, including the subpopulation identified by the present inventor. See Example 1, below.

Another important aspect of the invention is the reprogramming to a stem cell state of the above-mentioned diverse population, each cell of which can be expanded for analysis and selection (see Examples 2 and 3). The reprogramming should be accomplished in a manner that does not cause integration of any reprogramming genes into the genome of the cells or that otherwise limits regulatory approval of the cells for human therapeutic use.

A further important aspect of the invention is the selecting, from among the population of reprogrammed cells, the stem cells that have the unique property, first revealed by the inventor, of being a source for pharmaceutical grade surrogate pancreatic cells. The selection criteria differ from those for pluripotency, which is the goal of conventional methodology. As a consequence cells are obtained, pursuant to the invention, that are not pluripotent and yet have improved clinical utility (see Example 4).

The use of reprogramming genes to derive pluripotent stem cells is an inefficient process, resulting in the reprogramming of only 0.01 to 0.0001% of cells that meets the criteria of pluripotency. In the scientific literature these cells are referred to as "induced pluripotent stem cells" or iPS cells. In conventional approaches, cells that fail to meet the criteria for pluripotency are rejected; these cells are commonly denoted "incompletely reprogrammed" or "partially reprogrammed."

The genotype of a colony of iPS cells can contain a specific genetic variation that is present in the parent cell population at only a very low frequency. Accordingly, the process of reprogramming may identify and select for genotypes represented by only a small minority of the starting cell population.

From the facts (i) that reprogramming is an inefficient process and (ii) that iPS cell genotypes are frequently different from the typifying cell of the starting population, the present inventor surmised that a specific genetic alteration might predispose a cell to successful reprogramming to an iPS cell. Thus, the inventor perceived that cells previously rejected as incompletely reprogrammed could harbor a rare genetic alteration that predisposes them to a non-iPS cell phenotype, heretofore unrecognized as such, that nevertheless has value for the present therapeutic purpose.

Cell populations freshly harvested from human organs have a far greater range of cellular diversity than populations of cells cultured for an extended period of time. The inventor applied reprogramming genes to freshly harvested cell populations, in order to identify and select for a cell with a specific clinical utility, as mentioned above. A cell thus identified is not a pancreatic stem cell, as evidenced by the facts that identified cells (1) are not replicative and instead disappear in long-term culture, (2) do not exhibit stem cell morphology, and (3) can be isolated from tissues that do not contain putative pancreatic stem cells. (Putative pancreatic stem cells are hypothesized to exist in pancreatic ducts.) See Example 1, infra.

The cells of this invention that are harvested from the adult pancreas do not require serum for their isolation, do not exhibit stem cell morphology, and are not required to be isolated from specific fractions of purified pancreatic cell subpopulations. All of this contrasts sharply with what U.S. Pat. No. 8,377,689 describes, for example.

Pursuant to the invention, therefore, fresh human pancreas tissue can be used as a source of cells whence to identify and select a non-stem cell population that is predisposed to being a source for surrogate pancreatic cells, capable of treating insulin-dependent diabetes. In particular, as described in detail below, cells can be reprogrammed within one week of harvest from the organ to adopt stem cell state.

The resulting stem cells were selected on the basis of an ability (1) to differentiate efficiently to pancreatic endocrine progenitor cells, themselves amenable to treatment of insulin-dependent diabetes as described above, and (2) to survive and differentiate in minimal culture conditions that are both scalable and generally acceptable by regulatory authorities. "Efficiently" in this regard connotes producing a cell population at the end of the differentiation procedure that is comprised of at least about 80% endocrine progenitor cells; more preferably, at least about 90% endocrine progenitor cells. "Endocrine progenitor cells" are cells that will mature into the hormone-producing cells of the islets of Langerhans. These cells are characterized, for instance, by the simultaneous expression of the genes Pdx1, Nkx6.1 and NeuroD1. In this regard "survive" denotes an ability of at least about 80% of the starting viable cell population, and preferably at least about 90%, to be viable at the end of the differentiation procedure.

More specifically, compounds that drive differentiation towards the endoderm lineage are toxic to pluripotent stem cells. Conventional protocols employ serum to enhance cell survival, therefore; with serum, cell survival can exceed 50%. Serum is an undefined reagent, however, which generally is undesirable to regulatory agencies for the culture of human therapeutic cells.

In contrast to conventional protocols, the approach of the present invention eliminates serum, whereby the resulting cells could be considered suitable for a human cell therapy. Also, conventional protocols employ wnt, a growth factor that is expensive and extremely labile. The invention has eliminated the use of wnt, thereby to provide a process that is consistent and scalable.

Eschewing the use of both serum and wnt, the inventive methodology is ineffective at driving efficient differentiation of a pluripotent stem cell. On the other hand, the cells of a composition according to the invention are selected to respond to and survive this novel approach. Thus, more than about 80% of cells selected in accordance with invention, preferably more than about 90% of cells, survive the differentiation procedure. Further, of the surviving cells more than about 80%, and preferable more than about 90%, simultaneously express Pdx1, Nkx6.1 and NeuroD1, markers of the pancreatic endocrine lineage (see Example 3, last paragraph).

During the identification and selection procedure of this invention, the selection criteria for pluripotent stem cells are ignored, and the cells created pursuant to the invention indeed are not pluripotent; that is, they lack the ability to differentiate substantially to a non-pancreatic lineage. "Substantially" in this context means at least about 5%, preferably at least about 10%, and more preferably at least about 20% of the population of differentiated cells demonstrates characteristics specific to a non-pancreatic lineage.

For instance, cells produced per the invention were subjected to a protocol commonly used to derive a mixture of the three lineages, mesodermal, endodermal, and ectodermal. To demonstrate an ability to differentiate into a mixture of the three lineages, it is conventional practice to provide a media that does not cause the differentiation of one lineage in favor of another, such as serum, to a suspension of stem cell clusters, which enables spontaneous growth and differentiation. Under such culture conditions the stem cell clusters will differentiate according to their genetic programming, not specifically guided by provided culture conditions. The clusters thus formed are called "embryoid bodies" for their resemblance to an early mammalian embryo. See Rust (2006). Pluripotent cells will produce embryoid bodies that contain, after the fashion of a mammalian embryo, all three germ layers: the ectoderm, endoderm, and mesoderm. Unlike pluripotent stem cells, however, the mixture created from cells of the present invention did not include cells of the mesodermal lineage (see Example 4, e.g., in the fifth paragraph).

Cells of the invention also were subjected to a protocol commonly employed to differentiate pluripotent stem cells to cardiomyocytes, which are cells of the mesodermal lineage. Again in contrast with pluripotent stem cells, the cells of the invention failed to express cardiomyocyte-related genes in response to the differentiation protocol. Visual examination revealed that none of the cells described by this invention displayed the typical beating morphology of cardiomyocytes. Thus, less than about 5% of cells responded to a protocol used in the field to derive cardiomyocytes from pluripotent stem cells (see Example 4, e.g., in its sixth and seventh paragraphs)

The stem cells created in accordance with the present invention have the following properties, not described heretofore:

constitute a renewing stem cell population derived from a fresh human pancreas;

are predisposed to differentiate efficiently into substantially pure populations (i.e., ≥80% or ≥90%) of surrogate pancreatic cells capable of treating insulin-dependent diabetes;

are lacking in genomic integration of exogenous genes; and derived, reprogrammed, and cultured using reagents and processes that are generally considered acceptable for human use by regulatory agencies.

The surrogate pancreatic cells obtained pursuant to the invention also have properties that have not been described previously. These properties are:

constitute a substantially pure population of therapeutic cells (i.e., ≥80% or ≥90%), uncontaminated by stem cells with tumorigenic potential;

were differentiated using reagents and processes that generally are considered acceptable for human use by regulatory agencies and that are scalable; and lack genomic integration of exogenous genes B. Guidance on Implementing Inventive Approach 1. Obtaining Native Pancreatic Cells without Sacrificing Diversity Current methods for harvesting cells from organs cause the cells to be cultured over time. As a result, a subpopulation of proliferative cells that are suited to the culture conditions are favored, overtaking the population to create a homogeneous cell culture. This phenomenon, often denoted "culture drift," occurs in as few as ten population doublings.

In contrast, the present invention specifies that cells harvested from a mature organ cannot be cultured over a long term, preferably one week or less, with fewer than 5 population doublings. This prevents the cell population from adapting to the culture conditions and minimizes the opportunity for fast-growing cells to overtake the population and reduce overall population diversity.

2. Reprogramming Cells without Integration or Long-Term Expression of Reprogramming Genes Four genes, Oct4, Sox2, Klf4, and Myc, will cause a mature cell to adopt the properties of a stem cell. These "reprogramming genes" must be expressed in the same cell to be reprogrammed, and they are commonly delivered via viruses that insert the genes into the host genome, where they may be expressed.

Cells that have genes randomly inserted into their genomes are generally not accepted by regulatory authorities for transplant to humans. This is so because the cells thus modified present a higher risk of tumorigenicity than do non-manipulated cells.

The present invention entails delivering reprogramming genes in plasmids that do not integrate the genes into the genome and, hence, that effects their expression only temporarily. While in the nucleus the genes carried by a plasmid can be transcribed by the host nuclear transcription complexes. See Takacs (2010).

In a preferred embodiment, the genes are delivered in episomal plasmids. "Episomal" qualifies plasmids that can persist in the nucleus of a cell but that are not incorporated into any chromosome of the cell (Takacs, supra). Over time episomal plasmids are diluted from the cell population because they are not replicated and segregated during mitosis. Also, episomal plasmids can be expunged from the nucleus or can be degraded.

A myc family member commonly used for reprogramming, C-myc, is a known oncogene. In a preferred embodiment, the present invention employs L-myc, which is not an oncogene, in lieu of C-myc. See Nakagawa (2010).

3. Selection of Cells with Therapeutic Utility

Cells that are reprogrammed are distinguishable from non-reprogrammed cells by displaying typical stem cell morphology. Typical stem cells are small and round, have a prominent nucleus and a small cytoplasm, and grow in tight clusters.

A relatively small but discernable fraction of these reprogrammed cells are the source for pharmaceutical-grade surrogate pancreatic cells, pursuant to the present invention. This fraction is identified by virtue of satisfying the criteria detailed below.

- an ability to proliferate in culture conditions comprised of defined, non-animal-origin components
- an ability to respond to a minimal differentiation protocol by differentiating into a substantially pure population of pancreatic cells, i.e., a population comprised of at least about 80%, preferably at least about 90%, of cells that express genes characteristic of pancreatic endocrine progenitors and that can mature into hormone-producing cells of the islets of Langerhans
- The inventive protocol is designed to drive affected cells along a differentiation pathway that recapitulates the pathway that stem cells of the human body would follow in the development of the pancreas. Accordingly, the protocol mimics human development faithfully enough to produce a pancreatic cell that is indistinguishable from a pancreatic cell that can be isolated from a developing human fetus or neonate. In contrast to conventional techniques, the protocol according to the invention also uses only defined, non-animal origin components that can be part of a scalable pharmaceutical-grade manufacturing process. That is, the inventive protocol employs neither serum, used heretofore to enhance cell survival, nor a wnt family member, a growth factor that is extremely labile and expensive.
- an ability of the population to survive the differentiation procedure such that a large population of pancreatic cells can be efficiently produced
- As noted, "survive" denotes an ability of at least about 80% of the starting viable cell population, and preferably at least about 90%, to be viable at the end of the differentiation procedure.

Selecting, in accordance with this invention, for cells that are predisposed to form pancreatic cells selects against cells that have the pluripotency characteristic of efficient maturation into all three lineages of the human body. In particular, cells constituting the above-mentioned fraction that meets these criteria are not pluripotent because they are unable to differentiate substantially into cells of the mesodermal lineage, i.e., at least about 5%, preferably at least about 10%, and more preferably at least about 20% of the population of differentiated cells demonstrate characteristics specific to the mesodermal lineage.

C. Examples

1. Harvest of Primary Pancreatic Cells Using Only Defined Reagents of Non-Animal Origin A human pancreas was rinsed thoroughly in DMEM supplemented with 5× antibiotic/antimycotic (Penicillin, Streptomycin, Amphotericin. Life Technologies). A small portion of the tissue was minced into fragments no larger 2 mm in diameter. The minced tissue was transferred to a 50 ml conical tube and allowed to gravity sediment (FIG. 1 A,B). Media was replaced with fresh DMEM supplemented with 5× antibiotic/antimycotic and incubated at room temperature for 5 minutes. Media then was replaced with Primary Culture Media, comprised of DMEM/F12, L-ascorbic acid-2-phosphate (64 mg/L), Na Selenium (14 µg/L), insulin (19.4 mg/L), $NaHCO_3$ (543 mg/L), Transferrin (10.7 mg/L), TGF beta1 (2 µg/L), bFGF (10 µg/L), heparin (50 µg/L), and hydrocortisone (100 nM). Media was adjusted to pH 7.4 and 340 mOSM.

A variation of the foregoing protocol employed Essential 8 medium (Life Technologies) supplemented with EGF (100 µg/L), thrombin (1 U/ml), and hydrocortisone (100 nM). In another variation, fractionated pancreas tissue purchased from Prodo Labs (Irvine, Calif.) was used in lieu of a whole human pancreas; that is, the pancreas tissue was fractionated into islet preparations and ductal preparations. In yet another variation, a skin punch biopsy was used. These variations did not effect any substantial change in the outcome.

Animal origin free collagenase, AFA grade (Worthington Biochemical) in the amount of 50 mg/ml was added to the medium, and the culture flask was placed overnight in a 37° C. humidified incubator. The following day the remaining cell clumps were broken apart by trituration. The solution was transferred to a conical tube and centrifuged for 4 minutes at 200XG. The media was aspirated and the cell pellet was re-suspended in Primary Culture Media. The cells then were transferred to a cell culture flask pre-coated with CELLstart (Invitrogen) and returned to the incubator. After 24 hours, cells had adhered to the dish and begun to proliferate (see FIG. 1, image C).

In a variation of this protocol, collagenase was replaced with 1× TrypLE Select (Life Technologies). In a further variation, CELLstart was replaced with dishes coated with 1× VitronectinXF (Stem Cell Technologies). No substantial change occurred in relation to either variation.

When the cell culture grew to near confluence over the growth surface, they were dissociated by the addition of TrypLE Select (Life Technologies), and harvested for reprogramming. This process, beginning with receipt of the pancreas, did not last longer than 9 days. Excess cells were cryopreserved in Synth-a-freeze CTS (Life Technologies), following manufacturers instructions. In a variation, effecting no substantial change, excess cells were cryopreserved in Primary Culture Media supplemented with 10% DMSO.

Figure 2:
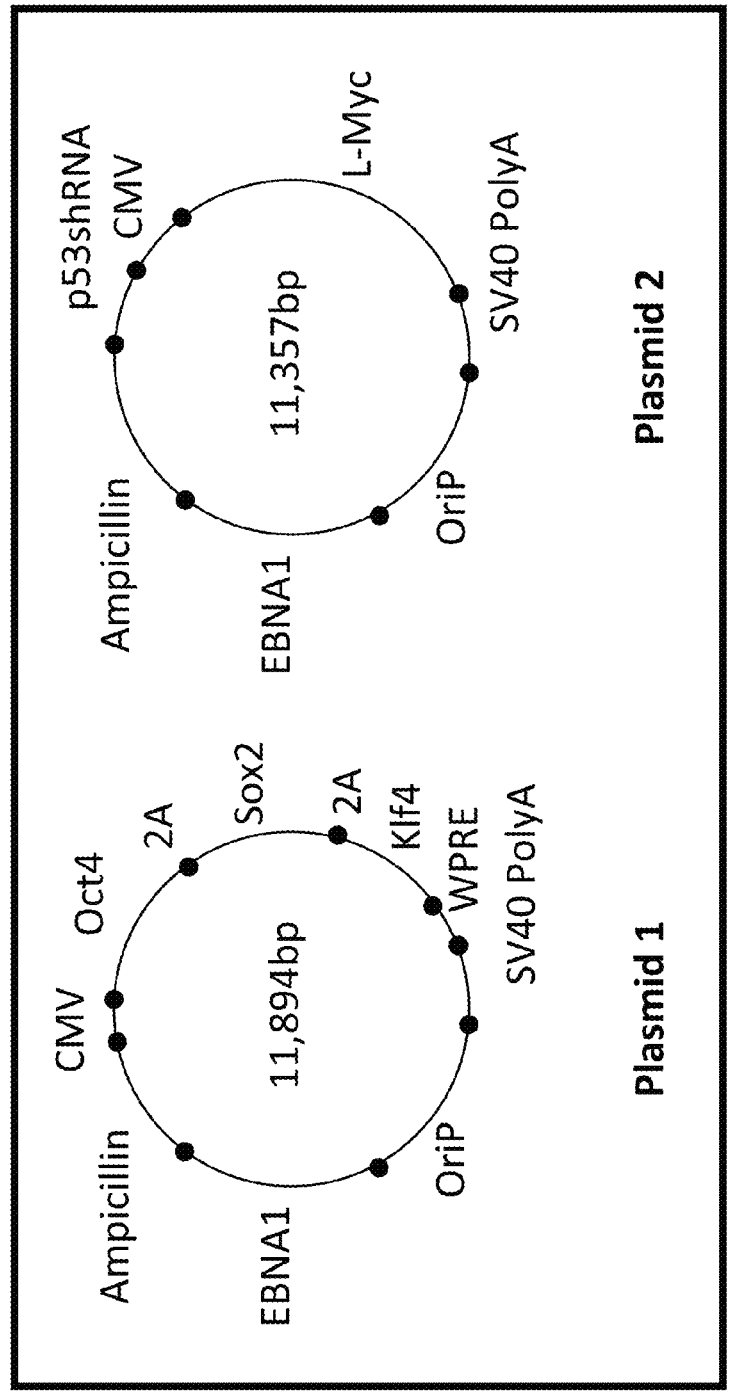
FIG. 2 illustrates schematically the organization of genes on reprogramming episomal plasmids. Abbreviations—CMV: cytomegalovirus promoter, 2A: self cleaving peptide sequence, WPRE: woodchuck hepatitis virus posttranscriptional response element, SV40 Poly A: polyadenylation signal, OriP: origin of replication, EBNA1: Epstein Barr nuclear antigen 1, p53shRNA: small hairpin RNA targeting p53.

2. Reprogramming of Pancreatic Cells Using Only Non-Integrating Gene Vectors and Defined Reagents of Non-Animal Origin Cell cultures were dissociated to single cells using TrypLE Select. The single cell suspension was counted using a hemacytometer. 1.5E6 cells were transferred to a new conical tube and centrifuged for 4 minutes at 200XG. The Pellet was resuspended in Solution V (Lonza), supplemented with 7.5 µg of reprogramming plasmid 1 and 12.5 µg of reprogramming plasmid 2 (FIG. 2), and was added to an electroporation cuvette. Reprogramming plasmids 1 and 2 are episomal, non-integrating plasmids. The genes used in the reprogramming plasmids have been described, for instance, by Takahashi (2006). L-myc was used in place of C-myc, a known oncogene. See Nakagawa (2010). The cuvette was inserted quickly into a Lonza Nucleofector and electroporated using program T-024.

The electroporated cells were diluted in Reprogramming Culture Media and transferred to dishes pre-coated with CELLstart. Reprogramming Culture Media was comprised of: DMEM/F12, L-ascorbic acid-2-phosphate (64 mg/L), Na Selenium (14 µg/L), insulin (19.4 mg/L), NaHCO$_3$ (543 mg/L), transferrin (10.7 mg/L), TGF beta1 (2 µg/L), bFGF (10 µg/L), and heparin (50 µg/L). Media was adjusted to pH 7.4 and 340 mOSM. Alternatively, the electroporated cells were diluted in Essential 6 media (Life Technologies) supplemented with 100 ng/ml bFGF (Sigma), 100 µM Sodium Butyrate (Sigma), and 100 nM Hydrocortisone (Sigma).

Figure 3:
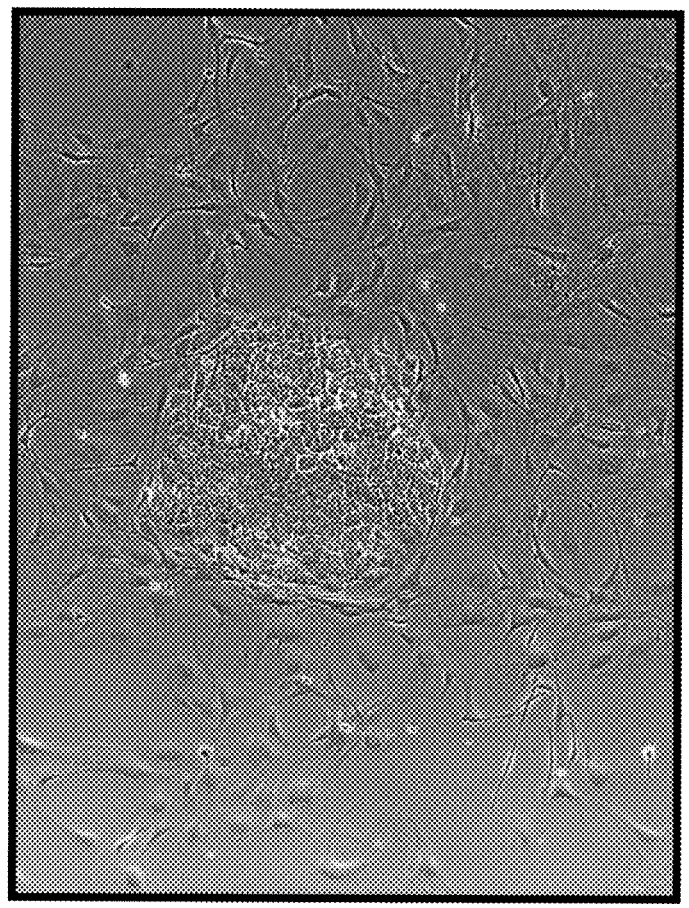
FIG. 3 presents a photomicrograph of reprogrammed cells. The phase contrast image shows that the cells exhibited stem cell morphology by 20 days after reprogramming.

The media was refreshed every 2 days. Optionally, the media was supplemented with 2 mM valproic acid (Sigma) during days 4-10. Cells were passaged when they had reached confluence, using TrypLE. By day 20 colonies of cells with stem cell morphology had appeared (FIG. 3).

3. Identification and Selection of Cells Useful for Treating Insulin-Dependent Diabetes Ten colonies of cells with stem cell morphology were manually dissociated from the substrate in small clumps of cells and were transferred to new tissue culture dishes, pre-coated with CELLstart, and were cultured with Reprogramming Culture Media. In a variation of this protocol, the colonies with stem cells morphology were transferred to tissue culture dishes pre-coated with Vitronectin XF (Stem Cell Technologies).

Figure 4:
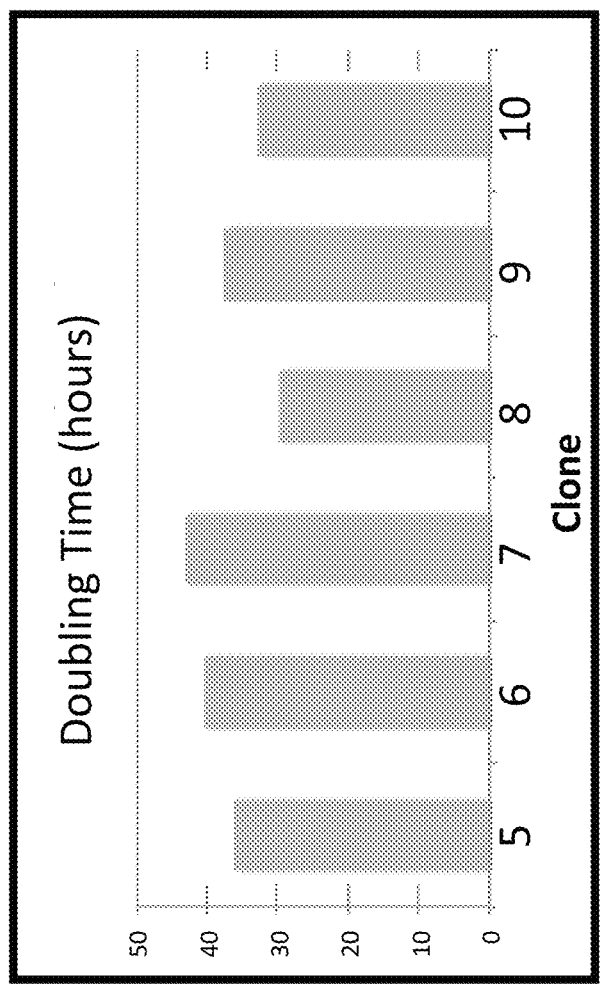
FIG. 4 is a bar graph that illustrates the proliferation in culture of cell colonies selected for their display of stem cell morphology. Ten colonies of cells resembling the stem cells shown in FIG. 3 were transferred manually to individual culture vessels. When the growth surface became covered by a confluent layer of stem cells, the cells were passaged to new culture vessels. The proliferation of the transferred cells was tracked over time by counting the number of cells present at the beginning and the end of three consecutive passages. Cell number was counted manually, using a hemacytometer, and the doubling time for each clone was calculated. Six of the ten selected clones were shown able to proliferate in minimal defined medium.

Of the ten colonies thus obtained, six continued to proliferate without a change in their morphology. The doubling time of the cell populations was calculated over passages 1-3 (FIG. 4).

Colonies of proliferating cells then were transferred to wells of six-well tissue culture dishes, pre-coated with CELLstart, and were allowed to grow to near confluence. At near-confluence the cells were subjected to a protocol to direct differentiation to the pancreatic lineage. Alternatively, cells were transferred to wells of a six-well tissue culture dishes pre-coated with Vitronectin XF (Stem Cell Technologies).

Novel protocol to drive differentiation of stem cells to the pancreatic lineage: The medium was replaced with DMEM/F-12 supplemented with 0.2% human serum albumin (HSA), 0.5XN2 (Life Technologies), 0.5XB27 (Life Technologies), 100 ng/ml Activin A, and 1 µM wortmannin (Sigma). The media was refreshed after 2 days. By day 4 the cells expressed genes characteristic of the endoderm lineage Sox17, HNF3β, and HNF4α. On day 5, the medium was replaced with IMDM/F-12 supplemented with 0.5% HSA, 2 µM retinoic acid (Sigma), 50 ng/ml Noggin, 10 ng/ml FGF7/KGF, and 0.5% insulin-transferrin-selenium (BD Biosciences). The medium was refreshed on day 7. On day nine, the medium was replaced with DMEM supplemented with 1% ITS, 1XN2, and 50 ng/ml EGF. The medium was refreshed on days 11 and 13. By day 15, the cells simultaneously expressed genes characteristic of pancreatic cells from which the endocrine pancreas is derived, Pdx1, Nkx6.1, and NeuroD.

Figure 5:
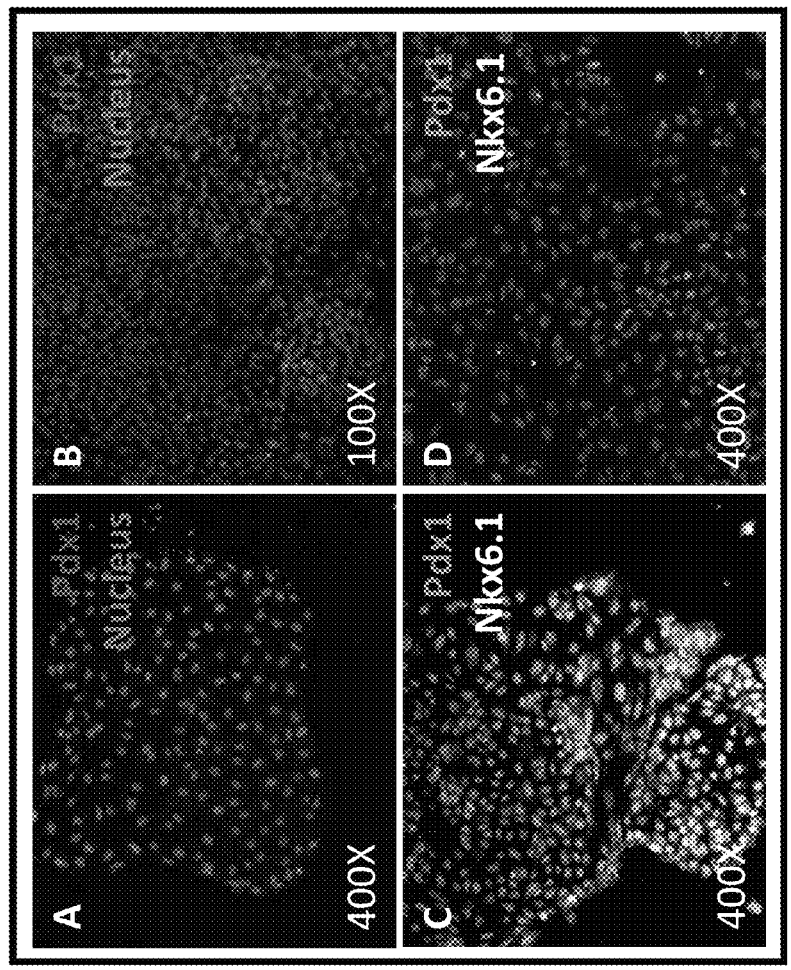
FIG. 5 presents photomicrographs A through D, depicting the results of selection applied to the above-mentioned six clones that proliferated in minimal defined medium. Two of the six clones survived the differentiation procedure, which employed minimal, defined reagents. Only a fraction (<50%) of cells of Clone 9 survived the differentiation, producing small rafts of cells in otherwise empty tissue culture dishes (A, C) Immunocytofluorescence revealed that Pdx1 was expressed in the nuclei of some of those cells (A), but appeared cytoplasmic in others (C). Nkx6.1 likewise appeared to be expressed in the nucleus (C). At least 80% of cells of Clone 10 survived the differentiation procedure, producing a confluent monolayer of cells (B, D) in the culture dishes. Pdx1 (B,D) and Nkx6.1 (D) were expressed in the nucleus of >90% of the cells. Therefore, only Clones 9 and 10 survived the differentiation procedure. Clone 9 survived poorly, and the cells did not appropriately express the pancreatic genes. This clone was rejected. Greater that 80% of the cells of Clone 10 survived the differentiation procedure, and greater than 90% of those cells expressed pancreatic genes appropriately. This clone was selected.

Of the six colonies only two were able to survive the differentiation procedure. Survival is defined as at least 80% of the cells subjected to the differentiation procedure remaining after differentiation. On day fifteen the two surviving cultures were fixed using 4% paraformaldehyde and prepared for immunocytofluorescence. The expression of the proteins Pdx1 and Nkx6.1 were visualized by primary incubation with anti-Pdx1 and anti-Nkx6.1 antibodies, and secondary incubation with fluorescence-coupled secondary antibodies. Of the two cultures only one maintained a nearly confluent culture composed of nearly exclusively Pdx1 and Nkx6.1 bi-positive cells (FIG. 5). Counting nuclei in several fluorescent images of clone 10 revealed that >95% of cells expressed Pdx1 and Nkx6.1.

4. Tests for Pluripotency

Clones 5-10 were differentiated to the three primary germ layers to determine if these stem cells were pluripotent. The differentiation protocol, commonly used by those practiced in the art, enables differentiation of stem cells into "embryoid bodies." See [Rust 2006]. Differentiation was evaluated by RT-qPCR analysis of gene expression.

Two wells of six-well dishes containing each of Clones 5-10 were cultured for five minutes in dispase (Stem Cell Technologies) and manually were dissociated by scraping with a pipette tip. Media containing cell clumps were transferred to a conical tube and centrifuged at 90XG for 5 minutes. Cell pellet was rinsed in DMEM (Gibco) and was resuspended in RPMI supplemented with 20% serum replacement (Invitrogen) and 0.5% vol/vol penicillin/streptomycin (Gibco).

Cell pellets were transferred to wells of a six well low-attachment dish and cultured for 15 days. Medium was changed every 2-3 days. Within two days, embryoid bodies had begun to form. Aliquots of embryoid bodies were harvested at days 0, 3, and 10 and were analyzed by RT-PCR. Total RNA was isolated using the RNeasy kit (Qiagen), treated with on-filter DNase and quantified by UV absorption. Pursuant to the manufacturer's instructions, a total of 1 µg of RNA was converted to cDNA, using Moloney murine leukemia virus (M-MuLV) reverse transcriptase (New England Biolabs) and random hexamer primers.

Quantitative PCR was performed with 50 ng of each reverse transcriptase reaction, 250 nM of each primer, and 1XSYBR green PCR master mix (Bio-RAD) and analyzed by iCycler thermocycler (Bio-RAD). Primers pairs are listed below in Table 1. Expression was calculated based on a standard curve, normalized to beta-actin, and made relative to day 0 (undifferentiated cells).

Table 1. Primers Used for RT-qPCR (Table 1 discloses SEQ ID NOS 1-26, respectively, in order of appearance)

TABLE 1

Primers Used for RT-qPCR
(Table 1 discloses SEQ ID NOS 1-26,
respectively, in order of appearance)

| Gene | Forward Primer | Reverse Primer |
|---|---|---|
| Oct4 | GGCAACCTGGAGAATTTGTT | GCCGGTTACAGAACCACACT |
| Nanog | TACCTCAGCCTCCAGCAGAT | TGCGTCACACCATTGCTATT |
| Sox17 | CCAGAATCCAGACCTGCACAA | CTCTGCCTCCTCCACGAA |
| AFP | GTAGCGCTGCAAACAATGAA | TCCAACAGCCTGAGAAATC |
| HNF3beta | GGAGCGGTGAAGATGGAA | TACGTGTTCATGCCGTTCAT |
| SHH | CCAATTACAACCCCTACATC | CAGTTTCACTCCTGGCCACT |
| Tbx6 | AGTGCTGAGGCCTACCTCCT | CCAGAAATGCAGCCGAGTAG |
| Nestin | GCCCTGACCACTCCAGTTTA | GGAGTCCTGGATTTCCTTCC |
| NeuroD | GCCCCAGGGTTATGAGACTA | GTCCAGCTTGGAGGACCTT |
| Nkx2.5 | AGGACCCTAGAGCCGAAAAG | GTTGTCCGCCTCGTCTTCT |
| GATA4 | GGAAGCCCAAGAACCTGAAT | GGGAGGAAGGCTCTCACTG |
| alphaMHC | ATTGCTGAAACCGAGAATGG | CGCTCCTTGAGGTTGAAAAG |
| beta Actin | CAATGTGGCCGAGGACTTTG | CATTCTCCTTAGAGAGAAGTGG |

Figure 6:
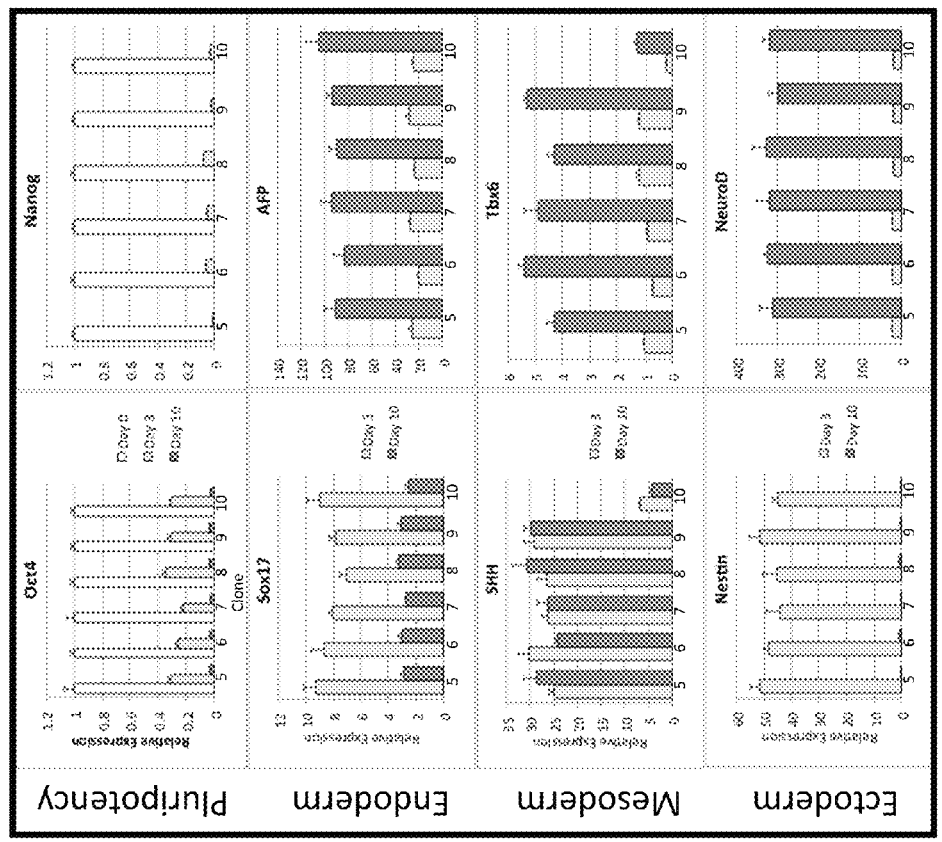
FIG. 6 includes bar graphs that depict results from RT-qPCR analyses of gene expression. Embryoid bodies from clones 5-9 expressed genes that are representative of endoderm, mesoderm, and ectoderm at days three and ten of differentiation. Clone 10 did not express genes representative of mesoderm, however. Concurrent with differentiation, all embryoid bodies down-regulated expression of pluripotency-related genes at days three and ten. Results are normalized to beta-actin and are shown relative to day 0 cultures (undifferentiated). Error bars represent standard deviation of three replicates.

A correlation was evident between high efficiency of differentiation to the pancreatic lineage, and low efficiency of differentiation to cells of the mesodermal lineage (FIG. 6). As differentiation progressed, all clones manifested reduced expression of pluripotency-related genes and increased expression in endodermal- and ectodermal-related genes. Clones 5-9 displayed an increase in mesodermal related genes. Clone 10 failed to demonstrate significant expression of mesodermal related genes.

To confirm this last result, clones 5 and 10 were subjected to a protocol designed to drive differentiation of pluripotent cells to mesodermal cardiomyocytes [Xu 2009]. In brief, clones were passaged onto low-attachment plates to form cell clusters as described above, except that Reprogramming Culture Media was used. After overnight incubation, media was replaced with media comprised of: DMEM, 1× non-essential amino acids (Gibco), 2 mM L-glutamine (Gibco), 5.5 µg/ml transferrin (Sigma), 5 ng/ml sodium selenite (Sigma), 0.1 mM beta mercaptoethanol (Gibco), and 1× penicillin/streptomycin (Gibco). Media was changed every 3 to 4 days.

Figure 7:
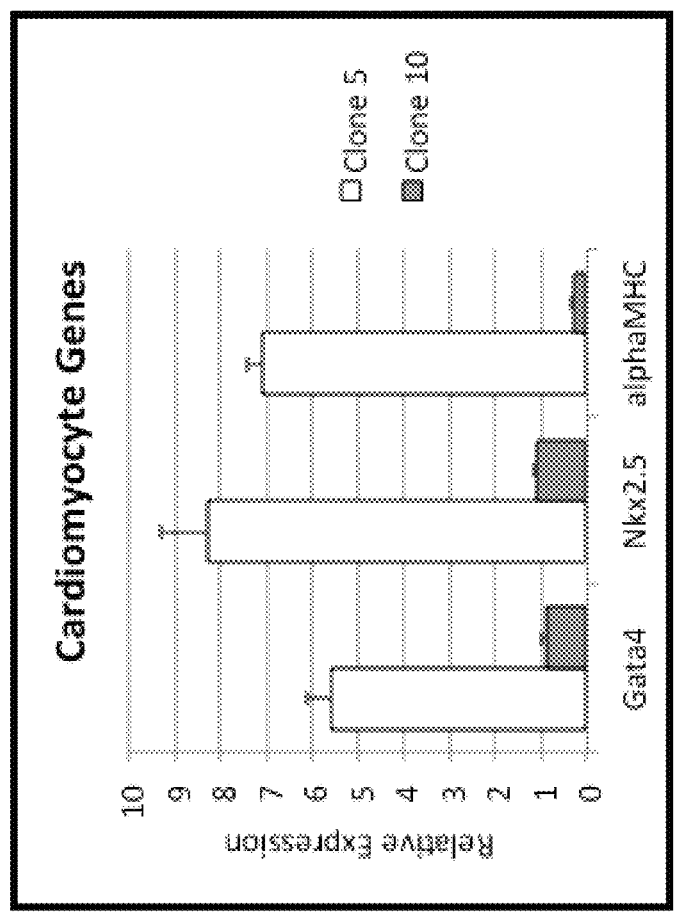
FIG. 7 presents a bar graph showing experimental results that confirm that Clone 10 was incapable of differentiation towards the mesodermal lineage. Clones 5 and 10 were directed to differentiate towards the mesodermal cardiomyocyte lineage, following a protocol that generates highly pure population of cardiomyocytes from pluripotent stem cells. See Xu (2009). At day 15, gene expression of cardiac specific growth factors (Gata4, Nkx2.5) and a structural protein (alpha MHC) were quantified by RT-qPCR. Clone 5 up-regulated expression of cardiac genes, while clone 10 maintained cardiac gene expression levels similar to undifferentiated cells. The results are presented as in FIG. 6 (see related commentary above).

Spontaneously beating cell clusters containing mesodermal cardiomyocytes appeared around day 12 in cultures of Clone 5. By day 15, at least 50% of the cell clusters were spontaneously contracting at one site, at least. Embryoid bodies were harvested at day 15, and RT-PCR analysis was carried out on genes representative of cardiomyocytes. Cardiomyocyte genes were expressed robustly by Clone 5, i.e., at least 5-fold compared to undifferentiated cells (FIG. 7). In contrast, spontaneously beating cell clusters were not present in the culture of Clone 10 at either day 12 or day 15 of differentiation. RT-PCR analysis of gene expression of cell clusters revealed that cardiomyocyte genes were not expressed above levels of undifferentiated stem cells.

Clone 10 thus was incapable of substantially differentiating to cells of the mesodermal cardiac lineage. Because no spontaneously beating cell clusters were identified, and because cardiomyocyte genes were not expressed at levels above undifferentiated cell populations, it was concluded that less than about 5% of cells responded to a protocol commonly employed to differentiate pluripotent stem cells to cardiomyoctes.

While particular embodiments of the subject invention have been discussed above, they are illustrative only and not restrictive of the invention. A review of this specification will make many variations of the invention apparent to those skilled in the field of the invention. The full scope of the invention should be determined by reference both to the claims below, along with their full range of equivalents, and to the specification, with such variations.

CITED PUBLICATIONS

U.S. Patent Documents

| | | |
|---|---|---|
| 6,436,704 B1 | August 2002 | Roberts and Mather |
| 6,815,203 B1 | November 2004 | Bonner-Weir and Taneja |
| 7,544,510 B2 | June 2009 | Habener et al. |
| 7,604,991 B2 | October 2009 | Bouwens and Baeyens |
| 8,110,399 B2 | February 2012 | Habener et al. |
| 2004/0115805 A1 | June 2004 | Tsang et al. |
| 8,377,689 B2 | February 2013 | Tsang et al. |

Other Publications

Shapiro, A. M. 2011 Curr Opin Organ Transplant 16(6), 627-31

Robertson, R. P. 2010 Endocrinol Metab Clin N Am 39, 655-67

Yamanaka, S. 2012 Cell Stem Cell 10, 678-84

Plath, K. 2011 Nat Rev Genet. 12(4), 253-65

Lai, M. I. 2011 J Assist Reprod Genet 28, 291-301

Stover, A. E., et al. 2011 Methods Mol Biol 767, 391-8

Kroon, E., et al. 2008 Nat Biotechnol 26(4), 443-52

Rezania, A., et al. 2012 Diabetes 61(8), 2016-29

Matveyenko, A. V., et al. 2010 Am J Physiol Endocrinol Metab 299, E713-20

Tahamtani, Y., et al 2013 Stem Cells and Dev 22(9), 1419-32

Title 21, U.S. Code of Federal Regulations, part 1271

Dor Y., et al. 2004 Nature 429(6987), 41-6

Pagluca, F. W. and Melton, D. A. 2013 Dev 140, 2472-83

Gong J, et al. 2012 J Mol Histol 43(6), 745-50

Noguchi H, et al. 2010 Cell Transplant 19(6), 879-86

Ciba P, et al. 2009 Ann Anat 191(1), 94-103

Dang T. T., et al. 2013 Biomaterials 34, 5792-801

Xu X. Q., et al. 2009 Stem Cells. 27(9), 2163-74

Rust W. L., et al. 2006 Stem Cells Dev 15(6), 889-904

Takacs M, et al. 2010 Biochim Biophys Acta 1799(3-4), 228-35

Nakagawa M, et al. 2010 Proc Natl Acad Sci USA 107(32), 14152-7

Takahashi K and Yamanaka S. 2006 Cell 126(4), 663-76

What is claimed is:

1. A composition comprising non-pluripotent progenitors of surrogate pancreatic cells, wherein the non-pluripotent progenitors comprise a varied population of native pancreatic cells that were harvested from a subject's pancreas, wherein the non-pluripotent progenitors have been cultured in only defined, non-animal origin reagents for fewer than five population doublings, and wherein the non-pluripotent progenitors are unable to differentiate into the mesodermal lineage, but can differentiate into surrogate pancreatic cells that are suitable for treating insulin-dependent diabetes.

2. The composition of claim 1, wherein the progenitors have the ability to proliferate in culture conditions comprises defined, non-animal-origin components.

3. The composition of claim 1, wherein the progenitors have no reprogramming genes integrated into their genomes.

4. The composition of claim 1, wherein the progenitors have the ability to respond to a minimal differentiation protocol by differentiating into a substantially pure population of pancreatic cells.

5. The composition of claim 4, wherein the substantially pure population of pancreatic cells comprises at least about 80% of cells that express genes characteristic of pancreatic endocrine progenitors and that can mature into hormone-producing cells of the islets of Langerhans.

6. The composition of claim 4, wherein the substantially pure population of pancreatic cells comprises at least about 90% of cells that express genes characteristic of pancreatic endocrine progenitors and that can mature into hormone-producing cells of the islets of Langerhans.

7. The composition of claim 1, wherein more than about 90% of cells comprising the composition express the markers Pdx1, Nkx6.1, and NeuroD1.

8. A composition comprising non-pluripotent progenitors of surrogate pancreatic cells, wherein the non-pluripotent progenitors have the ability to survive a differentiation protocol such that a large population of pancreatic cells can be efficiently produced, wherein the differentiation protocol comprises defined, non-animal-origin components, and wherein the non-pluripotent progenitors are unable to differentiate into the mesodermal lineage, but can be differentiated into surrogate pancreatic cells that are suitable for treating insulin-dependent diabetes.

9. The composition of claim 8, wherein the differentiation protocol does not comprise contacting the progenitors with a wnt family member.

10. The composition of claim 8, wherein the differentiation protocol comprises a first combination of components that drive differentiation to an endodermal lineage, whereby endodermal cells are obtained, and then exposing said endodermal cells to a combination of components that drive differentiation to a pancreatic endocrine lineage.

11. The composition of claim 8, wherein the progenitors have no reprogramming genes integrated into their genomes.

12. The composition of claim 8, wherein more than about 90% of cells comprising the composition express the markers Pdx1, Nkx6.1, and NeuroD1.

* * * * *